(12) United States Patent
Moriyama

(10) Patent No.: US 6,916,284 B2
(45) Date of Patent: Jul. 12, 2005

(54) ENDOSCOPE HOOD

(75) Inventor: Hiroki Moriyama, Tokyo (JP)

(73) Assignee: Olympus Corporation (JP)

( * ) Notice: Subject to any disclaimer, the term of this patent is extended or adjusted under 35 U.S.C. 154(b) by 30 days.

(21) Appl. No.: 10/685,864

(22) Filed: Oct. 15, 2003

(65) Prior Publication Data

US 2004/0077926 A1 Apr. 22, 2004

Related U.S. Application Data

(63) Continuation of application No. PCT/JP03/01190, filed on Feb. 5, 2003.

(30) Foreign Application Priority Data

Feb. 7, 2002 (JP) .................................... 2002-030970

(51) Int. Cl.⁷ ............................................... A61B 1/00
(52) U.S. Cl. ........................................ 600/127; 600/129
(58) Field of Search ........................ 600/121–124, 600/127, 129, 153

(56) References Cited

U.S. PATENT DOCUMENTS

| 3,794,091 A | * | 2/1974 | Ersek et al. ............... 150/154 |
| 4,825,259 A | * | 4/1989 | Berry, Jr. ................. 356/241.4 |
| 4,886,049 A | * | 12/1989 | Darras ........................ 600/124 |
| 5,674,181 A | * | 10/1997 | Iida ............................ 600/127 |
| 5,730,701 A | * | 3/1998 | Furukawa et al. .......... 600/127 |
| 5,788,628 A | * | 8/1998 | Matsuno et al. ............ 600/127 |
| 5,840,014 A | * | 11/1998 | Miyano et al. ............. 600/125 |

FOREIGN PATENT DOCUMENTS

| JP | 9-66019 | 3/1997 |
| JP | 2002-61760 | 3/2001 |
| JP | 2002-545 | 1/2002 |

OTHER PUBLICATIONS

International Search Report.

* cited by examiner

*Primary Examiner*—Beverly M. Flanagan
(74) *Attorney, Agent, or Firm*—Ostrolenk, Faber, Gerb & Soffen, LLP

(57) ABSTRACT

An endoscope hood of the present invention is provided with a cylindrical main hood body attached to an endoscope. The main hood body includes a fixing portion located substantially in a center. The fixing portion allows the inner circumferential surface of the main hood body to be forcibly fixed to the outer circumference of the distal end portion of the endoscope. The main hood body also includes a projection projected from the distal end portion of the main hood body and a non-fastened portion located at the rear end of the main hood body. The non-fastened portion is fitted with the outer circumference of the distal end portion of the endoscope without being fastened.

16 Claims, 3 Drawing Sheets

ENDOSCOPE HOOD

CROSS-REFERENCE TO RELATED APPLICATIONS

This is a Continuation Application of PCT Application No. PCT/JP03/01190, filed Feb. 5, 2003, which was not published under PCT Article 21(2) in English.

This application is based upon and claims the benefit of priority from the prior Japanese Patent Application No. 2002-030970, filed Feb. 7, 2002, the entire contents of which are incorporated herein by reference.

BACKGROUND OF THE INVENTION

1. Field of the Invention

The present invention relates to an endoscope hood attached to the distal end of an endoscope.

2. Description of the Related Art

When an internal cavity is observed using an endoscope, it sometimes happens that the objective lens at the distal end of the endoscope cannot be sufficiently away from a target object. To observe such an object, an endoscope hood having a substantially cylindrical shape is attached to the distal end of the insertion section of the endoscope. The hood is positioned between the target object and the objective lens disposed at the distal end of the endoscope. By so doing, a predetermined distance is maintained between the distal end of the endoscope and the target object, and reliable observation using the endoscope is thus enabled.

When the endoscope is being inserted into a body cavity or when it is being used for observation or treatment in the body cavity, the endoscope hood must not fall off the endoscope. As a measure for preventing the endoscope hood from falling off, the conventional art uses a tape. Specifically, after the endoscope hood is attached to the endoscope, the tape is wound around the attachment portion of the endoscope hood.

However, such a tape-winding operation takes time and very troublesome. In addition, since the tape-wound portion is inevitably thick, the endoscope may not be easily inserted into a body cavity.

In recent years, making an endoscope hood of an elastic material has come to be adopted as a measure for preventing the hood from falling off. The endoscope hood is forcibly fitted with the distal end of the microscope, utilizing the elasticity. In this case, the endoscope hood is provided with a fitting portion of sufficient length. When the fitting portion of the endoscope hood is elastically fitted with the distal end of the endoscope, with a sufficient length maintained, the endoscope hood is reliably prevented from falling off the endoscope body.

However, if the endoscope hood is elastically fitted with the distal end portion of the endoscope by force, it cannot be easily removed from the distal end of the endoscope. To be more specific, the endoscope hood may have to be removed from the endoscope by elastically deforming the endoscope hood by force and detaching it from the endoscope. Since the endoscope is subject to strong force then, it may be damaged.

The endoscope hood can be removed from the endoscope by engaging a fingernail with the distal end of the fitting portion of the endoscope hood and pulling the endoscope hood away from the endoscope. The endoscope hood can be removed by pulling the endoscope hood in the direction opposite to the fitting direction by means of a tool and separating the endoscope hood from the endoscope body. In such cases, however, the surfaces of the endoscope may be damaged.

The present invention has been made in consideration of the above problems, and an object of the present invention is to provide an endoscope hood which does not fall off the distal end of the endoscope after being fitted therewith, and which can be easily detached from the endoscope without giving damage to the endoscope.

BRIEF SUMMARY OF THE INVENTION

An endoscope hood according to the present invention comprises:

a cylindrical main hood body which has a central axis and is fitted around the outer circumferential surface of the distal end of the insertion section of an endoscope, the main hood body including:

a fixing portion located substantially in a center as viewed in an axial direction of the central axis, the fixing portion allowing the inner circumferential surface of the main hood body to be forcibly fixed to the outer circumference of the distal end of the endoscope;

a projection projected from the distal end of the main hood body, the projection being projected from the front face of the insertion section of the endoscope in the axial direction by a predetermined length in a state where the fixing portion is fixed to the outer circumference of the distal end of the endoscope; and a non-fastened portion located at a rear end of the main hood body, the non-fastened portion being fitted with the outer circumference of the distal end of the endoscope without being fastened.

After being fitted with the distal end of the endoscope, the endoscope hood of the present invention does not fall off the endoscope. In addition, the endoscope hood can be easily detached from the endoscope without giving any damage to the endoscope.

DETAILED DESCRIPTION OF THE INVENTION

Figure 1:
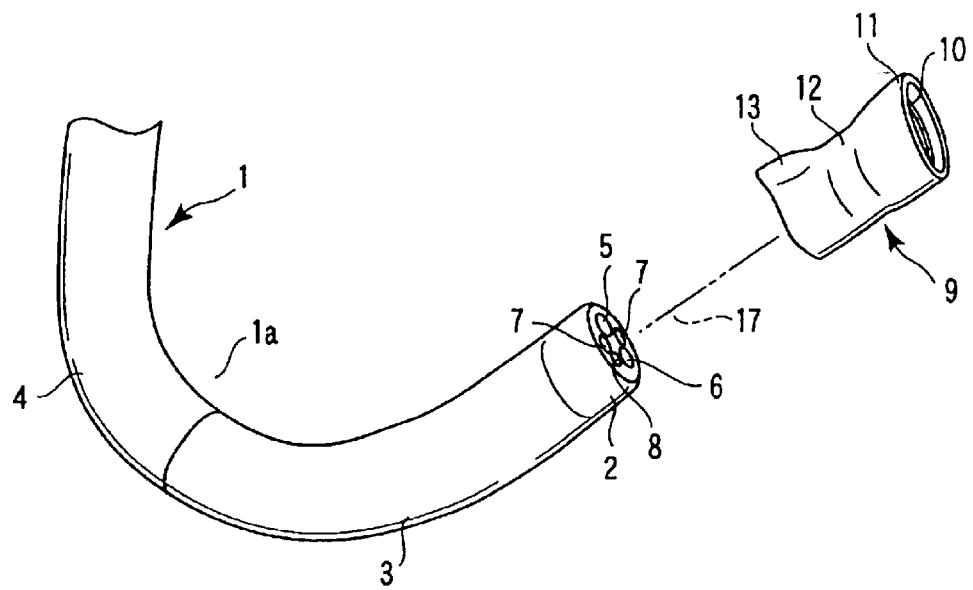
FIG. 1 is a perspective view showing an endoscope hood according to the first embodiment of the present invention, along with an endoscope with which the endoscope hood is fitted.
Figure 2:
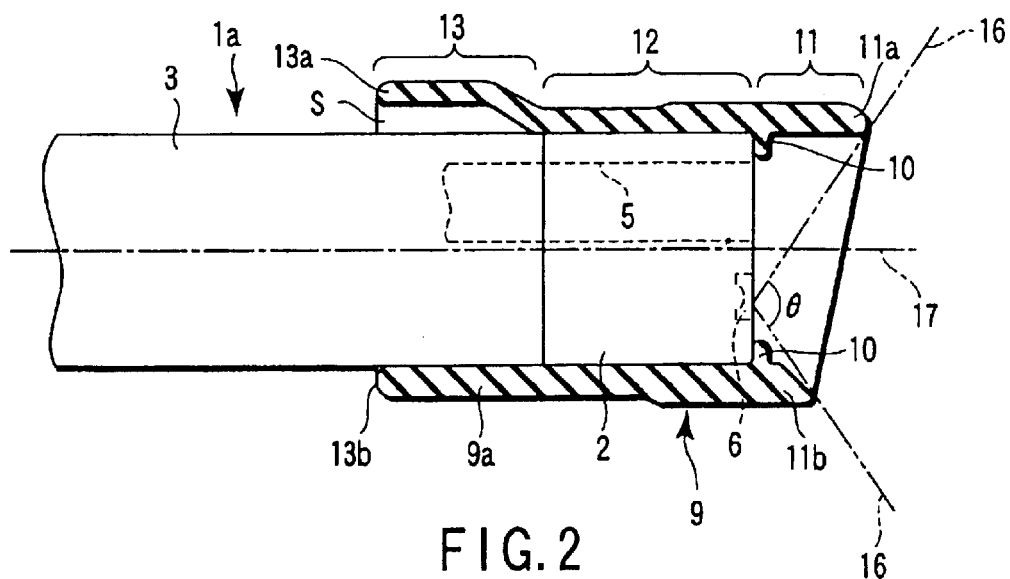
FIG. 2 is a longitudinal section showing how the endoscope hood of the first embodiment is fitted with the insertion section of the endoscope.

An embodiment of the present invention will now be described with reference to the accompanying drawings. FIGS. 1 and 2 illustrate the first embodiment of the present invention.

FIG. 1 shows an endoscope hood 9 according to the embodiment, and also shows an endoscope 1 with which the hood 9 is fitted. As shown in FIG. 1, the endoscope 1 comprises an elongated insertion section 1a adapted for insertion into a body cavity, and a proximal-side operation section (not shown) coupled to the proximal end of the insertion section 1a. The insertion section 1a includes an elongated, flexible soft portion 4 whose proximal end is coupled to the operation section. A distal end portion 2 is coupled to the distal end of the soft portion 4, with a curved portion 3 interposed. The curved portion 3 can be curved by remote control by operating the proximal-side operation section.

The distal end portion 2 includes an opening section serving as a large-diameter treatment tool insertion channel 5, an observation window 6, two illuminating windows 7, and a nozzle 8. The treatment tool insertion channel 5 and the observation window 6 oppose each other with respect to the central axis 17 of the insertion section 1a of the endoscope.

The treatment tool insertion channel 5 extends throughout the length of the insertion section 1a. An instrument tool (not shown) is inserted through the instrument tool insertion channel 5. The observation windows 6 are arranged on the optical axis of an observation optical system (not shown). Illuminating light emitted from an illuminating optical system (not shown) is guided to the two illuminating windows 7 and output from them. The nozzle 8 has an injection hole directed toward the observation windows 6, and a cleaning liquid is jetted out of the nozzle 8 to clean the observation windows 6.

FIG. 2 is a longitudinal section showing how the endoscope hood 9 of the present embodiment is fitted with the distal end portion 2 of the endoscope 1. As shown in FIG. 2, the endoscope hood 9 comprises a main hood body 9a having a cylindrical shape formed of an elastic material, such as rubber. The main hood body 9a has an annular abutment portion 10 that is projected inward from the inner peripheral surface of the distal end portion. The front face of the distal end portion 2 of the endoscope 1 strikes against the abutment portion 10. With this structure, when the endoscope hood 9 is fitted with the insertion section 1a of the endoscope 1, it is automatically positioned in the axial direction of the insertion section 1a of the endoscope 1. (This positioning determines an insertion amount [fitting amount] by which the insertion section 1a of the endoscope 1 is inserted into the endoscope hood 9.)

The distal end portion of the main hood body 9a is a projection 11. The projection 11 protrudes forward from the front end of the distal end portion 2 of the endoscope 1. The projection 11 is on the front side of the abutment portion 10 and is projected by a predetermined length. With this structure, the predetermined length is ensured between the front face (the objective lens) of the distal end 2 of the endoscope 1 and a living body (an object to be imaged).

The opening surface at the distal end of the projection 11 is a slanted surface, which is slanted at a predetermined angle with respect to a plane that is perpendicular to the central axis of the endoscope hood 9. In FIG. 2, reference numeral 11a denotes a long-axis portion of the projection 11, and that portion is longest in the axial direction. Reference numeral 11b denotes a short-axis portion of the projection 11, and that portion is shortest in the axial direction.

The main hood body 9a includes a fixing portion 12 and a non-fastened portion 13 which are located rearward of the abutment portion 10 and having predetermined lengths. The inner diameter of the fixed portion 12 is slightly smaller than the outer diameter of the distal end portion 2. With this structure, the fixing portion 12 of the main hood body 9a is elastically fitted around the outer circumferential surface of the distal end portion 2.

When the endoscope hood 9 is fitted around the distal end portion 2 of the endoscope 1, the abutment portion 10 serves to position the endoscope hood 9 with reference to the insertion section 1a of the endoscope 1 in the axial direction, as shown in FIG. 2. In the state shown in FIG. 2, the fixing portion 12 is elastically fitted around the outer circumferential surface of the distal end portion 2 of the endoscope 1. At the same time, the projection 11 axially protrudes from the front face of the distal end portion 2 of the endoscope 1 by a predetermined length.

The non-fastened portion 13 includes a convex portion 13a and a tight-contact portion 13b. The tight-contact portion 13b is in tight contact with the outer surface of the insertion section 1a. The convex portion 13a includes a finger-engagement portion located away from the outer circumference of the insertion section 1a.

The convex portion 13a and the tight-contact portion 13b have their centers align with the central axis of the endoscope hood 9, and the diameter of the former is greater than that of the latter. With this structure, the convex portion 13a defines a predetermined gap S with reference to the outer circumference of the insertion section 1a. The dimensions of the gap S are determined in such a manner as to enable the engagement of a finger with the convex portion 13a.

The convex portion 13a is not formed along all circumference of the non-fastened portion 13; it is formed only on part of the circumference. The area which the large-diameter convex portion 13a occupies in the non-fastened portion 13 should be as small as possible. With this structure, the insertion section 1a of the endoscope 1 can be inserted easily even when it is provided with the endoscope hood 9.

The convex portion 13a and the long-axis portion 11a of the projection 11 are substantially aligned with each other. With this structure, the convex portion 13a of the non-fastened portion 13 and the long-axis portion 11a of the projection 11 correspond to each other in light of their positions in the circumferential direction.

A description will now be given as to how the endoscope hood 9 of the above structure is attached or detached from the insertion section 1a of the endoscope 1.

First, a description will be given of the case where the endoscope hood 9 is attached to the distal end portion 2 of the endoscope 1. In this case, the endoscope hood 9 is forcibly fitted around the distal end portion 2 of the endoscope 1 while allowing the endoscope hood 9 to elastically expand and increase in diameter. The forcible insertion of the endoscope hood 9 is continued until the abutment portion 10 of the endoscope hood 9 strikes against the front face of the distal end portion 2 of the endoscope 1.

During the forcible insertion of the endoscope hood 9, the convex portion 13a of the non-fastened portion 13 is kept located on the same side as the treatment tool insertion channel 5 with respect to the central axis 17 of the insertion section 1a of the endoscope 1. To be more specific, the forcible insertion of the endoscope hood 9 is continued in such a manner that the circumferential position of the treatment tool insertion channel 5 agrees with the circumferential positions of the convex portion 13a of the non-fastened portion 13 and the long-axis portion 11a of the projection 11.

As can be seen from the above, when the endoscope hood 9 is assembled with the endoscope 1, the portions that are characteristic in terms of shape are used as positioning guides. Examples of such guide portions are the axially-extending long-axis portion 11a of the endoscope hood 9, the radially-protruding convex portion 13a, and the treatment tool insertion channel 15 (which is largest in diameter of the insertion section 1a of the endoscope 1). The endoscope hood 9 is positioned relative to the insertion section 1a of the endoscope 1 in the circumferential direction by making adjustments using these guide positions.

In the manner described above, the endoscope hood 9 is positioned relative to the insertion section 1a of the endoscope 1 in both the axial direction and the circumferential direction, and then fitted, as shown in FIG. 2. In the state shown in FIG. 2, the long-axis portion 11a of the projection 11 is located on the opposite side of the observation window 6 with respect to the central axis 17 of the endoscope insertion section 1a. On the other hand, the short-axis portion 11b of the projection 11 is located on the same side as the observation window 6 with respect to the central axis 17 of the endoscope insertion section 1a. Therefore, the field of observation 16 of the endoscope 1, which is obtained through the observation field 6 indicated by the two-dot-dash lines in FIG. 2, is least blocked by the projection 11. As a result, the viewing angle θ for observation, which is attained through the observation window 6 of the endoscope 1, can be as wide as possible.

When the endoscope hood 9 is removed from the distal end portion 2 of the endoscope 1, the following procedures are followed:

First of all, the operator inserts his or her finger into the gap S between the convex portion 13a of the non-fastened portion 13 and the outer circumferential surface of the distal end portion 2 of the endoscope 1 and brings it into engagement with the convex portion 13a. In this state, the endoscope hood 9 is pushed forward in the axial direction of the insertion section 1a of the endoscope 1 (i.e., in the direction in which the endoscope hood 9 is detached from the distal end portion 2 of the endoscope 1). Since the endoscope hood 9 is exerted with a compressive force acting in its axial direction, the rear end portion of the endoscope hood 9 expands radially. As a result, the endoscope hood 9 can be easily detached from the distal end portion 2 of the endoscope 1.

Alternatively, the operator may pull the convex portion 13a in such a manner as to raise it with his or her finger. In this case as well, the endoscope hood 9 can be easily detached from the distal end portion 2 of the endoscope 1. After being detached in this manner, the endoscope hood 9 may be cleaned and sterilized for reuse, or it may be disposed of.

The structure described above is advantageous in the following points. The endoscope hood 9 of the present embodiment comprises the fixing portion 12, the projection 11 and the non-fastened portion 13. Since the fixing portion 12 is forcibly fixed to the outer circumference of the distal end portion 2 of the endoscope 1, it prevents the endoscope hood 9 from falling off the distal end portion 2 of the endoscope 1.

Furthermore, in the state where the fixing portion 12 is forcibly fixed to the distal end portion 2 of the endoscope 1, the projection 11 axially protrudes from the front face of the insertion section 1a of the endoscope 1 by a predetermined length. Because of this protruding length, the projection 11 of the endoscope hood 9 serves to secure a predetermined distance between a living tissue (an object to be imaged) and the observation window 6 at the distal end of the endoscope 1.

Moreover, the non-fastened portion 13 is not pressed against the outer circumference of the insertion section 1a of the endoscope 1. In other words, it is not in tight contact with the outer circumference. When the endoscope hood 9 is detached from the distal end portion 2 of the endoscope 1, the operator is only required to bring his or her finger into engagement with the convex portion 13a of the non-fastened portion 13. By so doing, the operator can easily detach the endoscope hood 9. As can be seen from this, the endoscope hood 9 provided with the non-fastened portion 13 is advantageous in that it can be easily detached from the distal end portion 2 of the endoscope 1 without giving damage or leaving scratches on the endoscope 1.

In the present embodiment, the non-contact portion 13 is provided with only one convex portion 13a. Needless to say, the non-contact portion 13 may be provided with a plurality of convex portions 13a.

Figure 3:
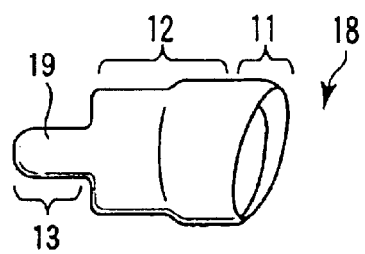
FIG. 3 is a perspective view of an endoscope hood according to the second embodiment of the present invention.

FIG. 3 shows an endoscope hood 18 according to the second embodiment of the present invention. Of the structural elements of the second embodiment, those which are similar to the structural elements of the first embodiment will be referred to by the same reference numerals as used in the description of the first embodiment (see FIGS. 1 and 2), and a repeated description of such elements will be omitted.

The endoscope hood 18 of the present embodiment comprises a non-fastened portion 13 made of a thin tongue portion 19. The tongue portion 19 is not formed throughout the circumference of the endoscope hood 18; it protrudes rearward in the axial direction from the fixing portion 12.

The tongue portion 19 is not pressed against the outer circumference of the distal end portion 2 of the endoscope 1. It is simply in contact with the outer circumference of the distal end portion 2 of the endoscope 1, and in this state, it is held. The tongue portion 19 can be easily raised whenever necessary.

When the endoscope hood 18 is detached from the distal end portion 2 of the endoscope 1, the operator pulls up the tongue-like member 19 of the present embodiment with his or her finger. By so doing, the operator can easily detach the endoscope hood 18 from the distal end portion 2 of the endoscope 1.

As in the first embodiment, the second embodiment is advantageous in that the endoscope hood 18 can be easily detached from the distal end portion 2 of the endoscope 1 without giving damage or leaving scratches on the endoscope 1.

Figure 4:
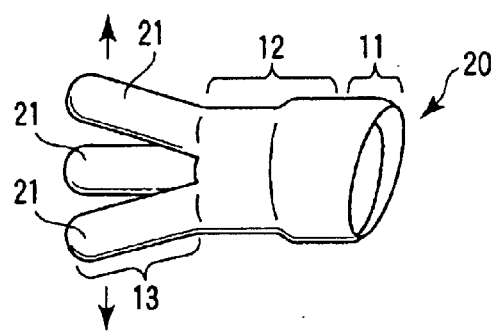
FIG. 4 is a perspective view of an endoscope hood according to the third embodiment of the present invention.
Figure 5:
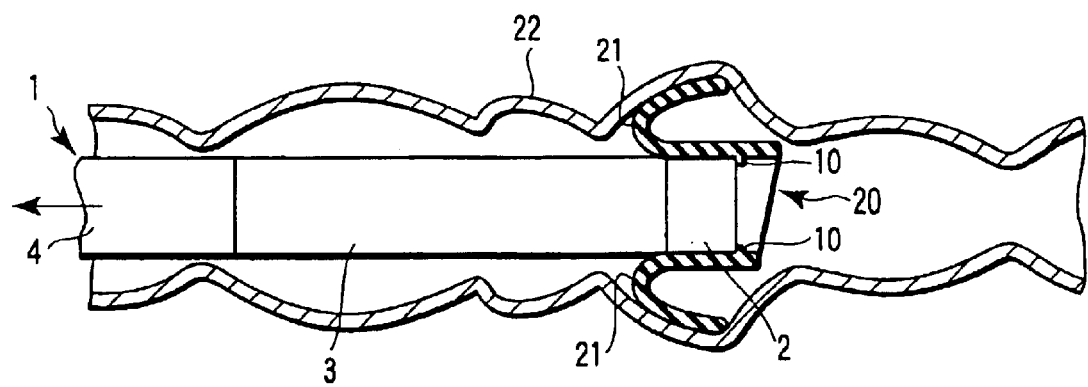
FIG. 5 is a longitudinal section illustrating an example in which the endoscope hood of the third embodiment is used.

FIGS. 4 and 5 show the third embodiment of the present invention. Of the structural elements of the third embodiment, those which are similar to the structural elements of the first embodiment will be referred to by the same reference numerals as used in the description of the first embodiment (see FIGS. 1 and 2), and a repeated description of such elements will be omitted.

FIG. 4 shows an endoscope hood 20 of the present embodiment. The endoscope hood 20 of the embodiment is provided with a plurality of tongue portions 21 (e.g., three tongue portions) arranged in the circumferential direction, forming the non-fastened portion 13. The tongue portions 21 constitute a non-fastened portion 13. Each tongue portion 21 protrudes rearward in the axial direction from the fixing portion 12.

When the fixing portion 12 is fitted or fixed to the insertion section 1a of the endoscope, the rear end portion of each tongue portion 21 is in the floated state from the outer circumference of the distal end portion 2 of the endoscope 1.

To detach the endoscope hood 20 of the present embodiment from the distal end portion 2 of the endoscope 1, the operator takes hold of all tongue portions 21 with both hands. Then, the operator raises and pulls them in such a manner as to expand them radially, as indicated by the arrows in FIG. 4. In this state, the endoscope hood 20 is moved in the axial direction relative to the distal end portion 2 of the endoscope 1. As a result, the endoscope hood 20 can be easily detached from the distal end portion 2 of the endoscope 1.

As in the first embodiment, therefore, the third embodiment is advantageous in that the endoscope hood 20 can be easily detached from the distal end portion 2 of the endoscope 1 without giving damage or leaving scratches on the endoscope 1.

In the case of the third embodiment, a plurality of tongue portions 21 are in the floated state from the outer circumference of the distal end portion 2 of the endoscope 1. Since the tongue portions 21 serve to expand the inner diameter of the endoscope hood 20 at a plurality of positions, the endoscope hood 20 can be detached from the distal end portion 2 of the endoscope 1 very easily.

FIG. 5 shows an example of a manner in which the endoscope 1 provided with the endoscope hood 20 of the present embodiment is used. FIG. 5 illustrates how the insertion section 1a of the endoscope 1 is inserted into the large intestine 22, which is long and winding, and is then pulled from inside the large intestine 22.

In general, the insertion section 1a of the endoscope 1 is inserted into the large intestine 22 as follows: The insertion section 1a of the endoscope 1 is inserted into the large intestine 22 by a predetermined length, and thereafter it is pulled back together with the large intestine 22. The large intestine 22 is pulled back in such a manner as to be folded. In the state where the large intestine 22 is folded, the insertion section 1a of the endoscope 1 is inserted into the large intestine 22 again by a predetermined length. With this process repeated, the insertion section 1a of the endoscope 1 is inserted further and further into the large intestine 22 while passing through the bending portions of the large intestine 22.

In the case where the endoscope hood 20 is not provided with a plurality of tongue portions 21, such as those of the third embodiment, the insertion section 1a of the endoscope 1 may not be reliably inserted into the interior of the large intestine 22. To be more specific, when the insertion section 1a of the endoscope 1 is pulled back, it may slip along the inner wall of the large intestine 22. If this happens, the inner wall of the large intestine 22 cannot be pulled in the intended direction together with the insertion section 1a of the endoscope 1. It is therefore likely that the insertion section 1a of the endoscope 1 will move relative to the inner wall of the large intestine 22 and come out of the large intestine 22.

Where the endoscope hood 20 of the present embodiment is attached to the endoscope 1, and the insertion section 1a of this endoscope 1 is inserted into the large intestine 22, the following advantages are obtained:

The endoscope hood 20 of the present embodiment is provided with a plurality of tongue portions 21 that are in the floated condition from the insertion section 1a of the endoscope 1. When the insertion section 1a of the endoscope 1 is pulled, the tongue portions 21, which are in contact with the inner wall of the large intestine 22 until then, are turned up and come into frictional engagement with the inner wall, as indicated by an arrow in FIG. 5. Because of the frictional engagement between the tongue portions 21 and the inner wall of the large intestine 22, the large intestine 22 can be pulled in the folded state.

The insertion section 1a of the endoscope 1 does not move relative to the large intestine 22, nor does it slip off the large intestine 22. As can be understood from this, the tongue portions 21 of the endoscope hood 20 of the present embodiment not only contribute to easy detachment of the endoscope hood 20 but also enhance the usability when the insertion section 1a of the endoscope 1 is inserted into the large intestine 22.

When the insertion section 1a of the endoscope 1 is pushed into the large intestine 22, the tongue portions 21 are not turned up. The insertion section 1a of the endoscope 1 can therefore be inserted into the large intestine 22 without any obstruction.

The tongue portions 21 are three in number in the present embodiment. They may be two, or they may be four or more.

Figure 6A:
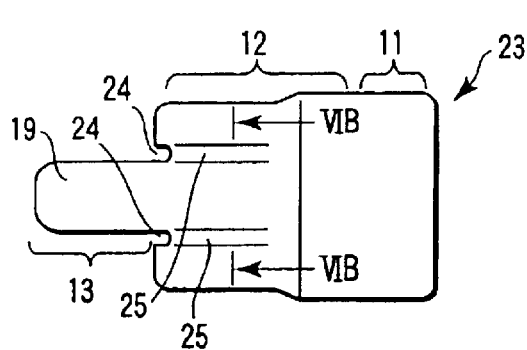
FIG. 6A is a plan view of an endoscope hood according to the fourth embodiment of the present invention.
Figure 6B:
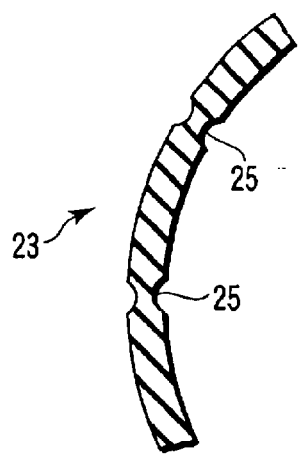
FIG. 6B is a section taken along line VIB—VIB of FIG. 6A.

FIGS. 6A and 6B illustrate the fourth embodiment of the present invention. The endoscope hood 23 of the present embodiment is a modification of the endoscope hood 18 of the second embodiment (see FIG. 3). In the description below, therefore, the structural elements that are similar or correspond to those of the second embodiment will be referred to by the same reference numerals as used in the second embodiment, and a detailed description of such structural elements will be omitted herein.

As shown in FIG. 6A, the endoscope hood 23 of the present embodiment has notches 24 at connecting portions between a fixing portion 12 and a tongue portion 19 of a non-fastened portion 13. To be more specific, the notches 24 are formed in the proximal portions on the respective sides of the tongue portion 19. U-shaped grooves 25 extend axially from the notches 24 and terminate at an intermediate position of the fixing portion 12. As shown in FIG. 6B, the U-shaped grooves 25 are formed on both surfaces of the fixing portion 12. Thin portions of the fixing portion 12 are formed by the U-shaped grooves 25.

When the tongue portion 19 of the endoscope hood 23 of the present embodiment is pulled in the axial direction in such a manner that the tongue portion 19 is turned up, the thin portions defined by the U-shaped portions 25 split axially from the notches 24. Since the fixing portion 25 is therefore split off, the endoscope hood 23 can be easily detached from the insertion section 1a of the endoscope 1. After being broken and detached in this manner, the endoscope hood 23 is disposed of.

The endoscope hood 23 of the present embodiment produces similar advantages to those of the second embodiment. In addition, the endoscope hood 23 need not be subject to the cleaning and sterilizing operation, which is a troublesome operation in practice.

The U-shaped grooves 25 may be formed throughout the fixing portion 12 or the endoscope hood 23. That is, the U-shaped grooves 25 are not limited to any particular length as long as they ensure splitting and enable the endoscope hood 23 to be easily detached from the insertion section 1a of the endoscope 1.

Figure 7:
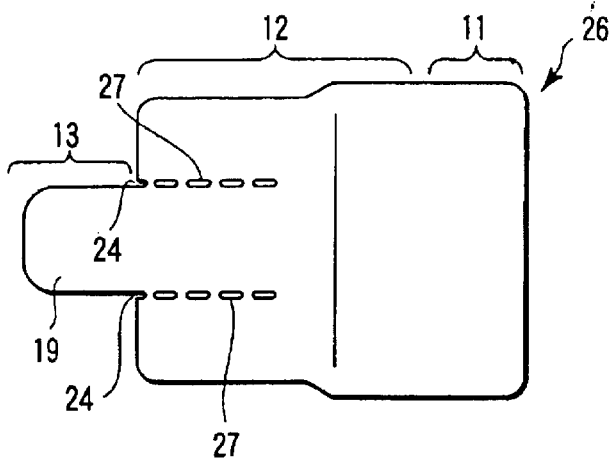
FIG. 7 is a plan view of an endoscope hood according to the fifth embodiment of the present invention.

FIG. 7 shows an endoscope hood 26 according to the fifth embodiment of the present invention. The endoscope hood 26 of the present embodiment is a modification of the endoscope hood 23 of the fourth embodiment (see FIGS. 6A and 6B). In the description below, therefore, the structural elements that are similar or correspond to those of the fourth embodiment will be referred to by the same reference numerals as used in the fourth embodiment, and a detailed description of such structural elements will be omitted herein.

The endoscope hood 26 of the present embodiment comprises perforations 27 in place of the U-shaped grooves 25 of the endoscope hood 23 of the fourth embodiment. In the other points, the endoscope hood 26 of the present embodiment is similar in structure to that of the fourth embodiment.

When the tongue portion 19 of the endoscope hood 26 of the present embodiment is pulled in the axial direction in such a manner that the tongue portion 19 is turned up, the perforations 27 split axially. Since the fixing portion 12 is therefore split off, the endoscope hood 23 can be easily detached from the insertion section 1a of the endoscope 1. Hence, the endoscope hood 26 of the present embodiment produces similar advantages to those of the fourth embodiment.

Figure 8:
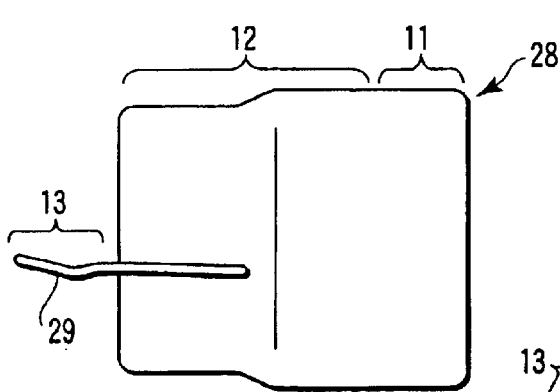
FIG. 8 is a plan view of an endoscope hood according to the sixth embodiment of the present invention.

FIG. 8 shows an endoscope hood 28 according to the sixth embodiment of the present invention. In the description below, the structural elements that are similar or correspond to those of the first embodiment (FIGS. 1 and 2) will be referred to by the same reference numerals as used in the first embodiment, and a detailed description of such structural elements will be omitted herein.

The non-fastened portion 13 of the endoscope hood 28 of the present embodiment is a string member 29 made of a silk string, for example. One end portion of the string member 29 is embedded in the peripheral wall of the fixing portion 12. The embedded portion of the string member 29 extends in the axial direction of the fixing portion 12, is substantially linear, and has an appropriate length.

The other end portion of the string member 29 is exposed and protrudes rearward from the fixing portion 12. The protruding portion extends rearward in the axial direction.

To detach the endoscope hood 28 of the present embodiment from the distal end portion 2 of the endoscope 1, the exposed portion of the string member 29 is taken hold of and pulled forward in the axial direction (i.e., in the direction toward the fixing portion 12). By so doing, the embedded portion of the string member 29 is pulled out, splitting the fixing portion 12. As a result, the endoscope hood 23 can be easily detached from the insertion section 1a of the endoscope 1.

After being broken and detached in this manner, the endoscope hood 28 is disposed of. The endoscope hood 28 need not be subject to the cleaning and sterilizing operation, which is a troublesome operation in practice.

The string member 29 may be embedded in the fixing portion 12 throughout the length of the fixing portion 12 or endoscope hood 28. Alternatively, it may terminate at an intermediate position, as shown in FIG. 8.

Figure 9:
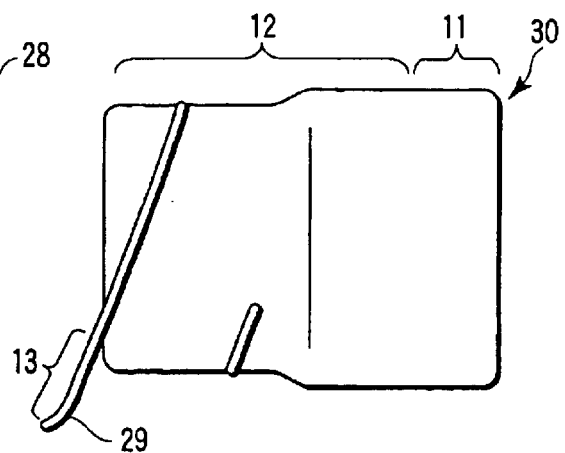
FIG. 9 is a plan view of an endoscope hood according to the seventh embodiment of the present invention.

FIG. 9 shows an endoscope hood 30 according to the seventh embodiment of the present invention. The present embodiment is a modification of the sixth embodiment (see FIG. 8). Structural elements that are similar or correspond to those of the sixth embodiment will be referred to by the same reference numerals as used in the fourth embodiment, and a description of such structural elements will be omitted.

In the endoscope hood 30 of the present embodiment, a string member 29, such as that of the sixth embodiment, is embedded in the fixing member 12 in such a manner that the embedded portion forms a spiral in the circumferential wall of the fixing portion 12.

To detach the endoscope hood 30 from the distal end portion 2 of the endoscope 1, the exposed portion of the string member 29 is taken hold of and pulled forward (i.e., in the direction toward the fixing portion 12), in such a manner that the spiral of the embedded portion is unwound. By so doing, the embedded portion of the string member 29 is pulled out, splitting the fixing portion 12. As a result, the endoscope hood 23 can be easily detached from the insertion section 1a of the endoscope 1.

The endoscope hood 30 of the present embodiment produces similar advantages to those of the sixth embodiment. The endoscope hood 30 of the present embodiment is especially advantageous in that the fixing portion 12 does not greatly split off in the axial direction even if the string member 29 is pulled partially by accident. Hence, the endoscope hood 30 is prevented from being undesirably detached from the insertion section 1a of the endoscope 1.

The present invention is advantageous in the technical field of endoscope hoods which are fitted with the distal ends of the elongated insertion sections of endoscopes to be inserted into body cavities. The present invention is also advantageous in the technical field in which such endoscope hoods are manufactured and used.

What is claimed is:

1. An endoscope hood comprising:
   a projection extending from a distal end portion of an insertion section of an endoscope, to separate an optical member for observation from an object to be imaged when the endoscope hood is fixed to the distal end portion of the insertion section of the endoscope;
   a fixing portion located proximally of the projection, an inner surface of the fixing portion configured to be pressed against a circumferential surface of the insertion section to fix the endoscope hood to the insertion section of the endoscope; and
   a non-fastened portion located proximally of the fixing portion, the non-fastened portion including a portion which is not fixed to the circumferential surface of the insertion section of the endoscope when the fixing portion is pressed against the outer circumference of the insertion section of the endoscope.

2. An endoscope hood according to claim 1, wherein the non-fastened portion includes at least one finger-engagement portion which defines a predetermined gap with reference to the circumferential surface of the insertion section of the endoscope when the endoscope hood is fixed to the distal end portion of the insertion section of the endoscope.

3. An endoscope hood according to claim 2, wherein the non-fastened portion includes: a convex portion projecting outwardly from the outer circumferential surface of the insertion section of the endoscope to define the predetermined gap with reference to the circumferential surface of the insertion section of the endoscope; and a portion which is in contact with the insertion section of the endoscope, the finger-engagement portion being formed by the convex portion.

4. An endoscope hood according to claim 1, wherein the non-fastened portion includes a tongue portion projected rearward from a rear end of the fixing portion.

5. An endoscope hood according to claim 1, wherein:
   the non-fastened portion includes a protrusion projected rearward from a rear end of the fixing portion; and
   the fixing portion includes a to-be-split portion along which the fixing portion is split off when the protrusion is turned up and pulled.

6. An endoscope hood according to claim 5, wherein the to-be-split portion is a thin portion of the fixing portion, the thin portion being thinner than other portions of the fixing portion.

7. An endoscope hood according to claim 5, wherein the to-be-split portion includes cutout sections formed in the fixing portion, the cutout sections including a notch directed rearward of the fixing portion, and a groove extending from the notch toward a distal end of the fixing portion.

8. An endoscope hood according to claim 5, wherein the to-be-split portion includes a U-shaped groove formed in the fixing portion, a portion of the fixing portion which defines a bottom of the U-shaped groove being thinner than other portions of the fixing portion.

9. An endoscope hood according to claim 5, wherein the to-be-split portion includes perforations, the perforations being holes formed in the fixing portion in a row extending in the axial direction.

10. An endoscope hood according to claim 1, wherein: the non-fastened portion includes a string member, the string member comprising an embedded portion embedded in the fixing portion, and a protrusion protruding rearward from a rear end portion of the fixing portion, and the fixing portion includes a to-be-split portion along which the fixing portion is split off when the protrusion is turned up and pulled.

11. An endoscope hood according to claim 2, wherein the projection includes a long-axis portion having a first projection length and a short-axis portion having a second projection length shorter than the first projection length, and the finger-engagement portion is formed at a position corresponding to the long-axis portion.

12. An endoscope hood, comprising:
   a projection extending from the a distal end portion of an insertion section of an endoscope to separate an optical member for observation from an object to be imaged when the endoscope hood is fixed to the distal end portion of the insertion section of the endoscope;
   an integral section formed integrally with the projection at a distal end side of the projection and located at an outer circumferential surface of the insertion section when the endoscope hood is attached to the insertion section of the endoscope, the integral section having a fixing portion configured to be pressed against the outer circumferential surface of the insertion section to attach the endoscope hood to the endoscope, and having a removing portion to permit the endoscope hood to be removed from the endoscope.

13. An endoscope hood according to claim 12, wherein the removing portion is formed of a convex portion for finger engagement, which defines a gap with reference to the outer circumferential surface of the insertion section of the endoscope.

14. An endoscope hood according to claim 12, wherein the removing portion includes a portion configured to be held by a user for removing the endoscope hood from the insertion end of the endoscope.

15. An endoscope hood according to claim 14, wherein at least a portion of the fixing portion includes a to-be-split portion configured to be split when the endoscope hood is removed from the insertion end of the endoscope.

16. An endoscope hood according to claim 13, wherein the projection includes a first part having a first projection length and a second part having a second projection length shorter than the first projection length, and the convex portion is formed at a position corresponding to the first part.

* * * * *